United States Patent [19]

Whitaker

[11] Patent Number: 4,816,573

[45] Date of Patent: Mar. 28, 1989

[54] SEPARATION OF CARRAGEENAN CONTAINING SEA PLANTS

[75] Inventor: R. John Whitaker, Prince Edward Island, Canada

[73] Assignee: Prince Edward Island Development Agency, Charlottetown, Canada

[21] Appl. No.: 801,579

[22] Filed: Nov. 25, 1985

[51] Int. Cl.$^4$ .............................................. A01G 7/00
[52] U.S. Cl. ................................... 536/128; 536/114; 536/122; 514/54; 260/705
[58] Field of Search ................... 514/23, 54; 536/128, 536/114, 122, 128; 260/705

[56] References Cited

U.S. PATENT DOCUMENTS 3,176,003 3/1965 Stancioff .............................. 260/209
3,879,890 4/1975 Chen et al. ............................ 47/1.4
4,112,223 9/1978 Lin et al. .............................. 536/114

OTHER PUBLICATIONS

McCandless et al., Planta, vol. 112, pp. 201-212 (1973).

Primary Examiner—Ronald W. Griffin
Assistant Examiner—Nancy S. Carson

[57] ABSTRACT

Sea plants containing kappa carrageenan are separated from those containing lambda carrageenan by subjecting a mixture of such plants to preferential hydration of the lambda plants without substantial dissolution of carrageenan, and separating it from the kappa plants by selection based on water content or on properties related to or dependent on water content.

8 Claims, No Drawings

SEPARATION OF CARRAGEENAN CONTAINING SEA PLANTS

This invention relates to separation of sea plants containing kappa carrageenan from sea plants containing lambda carrageenan.

Carrageenan, a polysaccharide hydrocolloid obtained from sea plants, has long been known to exist primarily in chemically different species: kappa-carrageenan which is caused to gel or precipitate from aqueous solution by the addition of potassium and certain other ions; and lambda-carrageenan, which remains soluble in aqueous solutions of potassium salts. Because of their differing gelling characteristics and their consequent different practical utilities it has become important to separate these two forms of carrageenan and to provide each of them in substantially pure form as an article of commerce. However, as sea plants occur in nature and as they are commonly harvested the plants contain varying proportions of kappa- and of lambda-carrageenan.

It has hitherto generally been the practice to process sea plants by extracting from them all of the carrageenan in the form of an aqueous solution, and subsequently precipitating and separating the kappa carrageenan from the lambda carrageenan, or by first selectively extracting the lambda carrageenan from the sea plants with certain aqueous salt solutions, and subsequently extracting the kappa carrageenan remaining in the plants, as described for example in Stancioff U.S. Pat. No. 3,176,003. It has also been reported that the haploid form of sea plants contains largely kappa-carrageenan and the diploid form largely lambda-carrageenan by McCandless et al., Planta, Vol. 112, 201-212 (1973); and it has been proposed in Chen et al., U.S. Pat. No. 3,879,890 to separate gametophytes from tetrasporophytes and propagate each vegetatively apart from the other in order to provide sea plants containing either kappa or lambda carrageenan preferentially. However, the haploid (gametophytic) and diploid (tetrasporophytic) plants are morphologically similar in the natural state and cannot readily be distinguished without microscopic examination of sections.

It has now been found that mixtures of lambda-carrageenan-bearing plants (hereinafter "lambda plants") and kappa-carrageenan-bearing plants (hereinafter "kappa plants") such as occur in nature, for example the genus *Chondrus crispus* (also called Irish moss) can be treated with certain aqueous media such that the lambda plants preferentially absorb water so that they become readily distinguishable and can be physically segregated from the kappa plants. Separation of the kappa plants and lambda plants can be carried out manually or by machine, after which the desired carrageenan can be extracted from each separately by conventional procedures.

The present invention features preferentially hydrating lamba-carrageenan-containing sea plants in admixture with kappa-carrageenan-containing plants without substantial dissolution of carrageenan, then separating the lambda plants from the kappa plants by selection based upon water content, i.e. upon properties related to or dependent on water content.

In another aspect the invention features contacting a mixture of kappa-carrageenan-containing and lambda-carrageenan-containing sea plants with a water solution at pH above about 10 containing a cation selected from the group consisting of ammonium, potassium, rubidium, cesium, calcium, barium, strontium and magnesium at a temperature from 5° to 95° C., the initial concentration of cation in said solution being above 0.0025 molar, until the water content of said lambda plants is from 4.5 to 15, preferably 4.5 to 7, times the bone-dry weight thereof and the water content of said kappa plants is no greater than 6, preferably 4, times the bone-dry weight thereof and less than that of said lambda plants, and separating the lambda plants from the kappa plants by selection based on water content.

In one embodiment the step of separating the lambda-carrageenan-containing plants from the kappa-carrageenan-containing plants is based upon their physical appearance and may be carried out manually in accordance with visual inspection. In another embodiment the separating step is carried out by winnowing, that is by subjecting the plant mixture to a stream of air, the kappa plants thus being blown away from the lambda plants. In still another embodiment the separating is carried out by impacting the mixture of weeds against a solid surface; the lambda plants adhere to the surface, while the kappa plants do not and can be selectively removed by gravity, by centrifugal force, or by an air stream. In still another embodiment the separating is carried out by sieving or straining, the lambda plants passing through the interstices of a sieve or strainer when subjected to pressure while the kappa plants do not. In general, the separating step is based upon the differing physical characteristics or water content of the lambda and kappa plants after preferential hydration.

By "bone dry weight" of sea plants is meant the value achieved by heating a sample of the plant in a circulating hot air oven at 70° C. until the sample achieves constant weight.

The process of the present invention makes it possible to segregate kappa carrageenan bearing plants from lambda carrageenan bearing plants without the need for elaborate processing equipment of the type needed for complete extraction and processing of the carrageenan. The hydration step can be carried out in vats or pits exposed to the air and conducted at ambient temperature without the need for heating equipment.

The cations present in the water solution can be any of ammonium, potassium, rubidium, cesium, calcium, barium, strontium or magnesium, of which potassium and calcium are preferred. The presence of any of these cations in water solution retards hydration of kappa plants and dissolution of the kappa-carrageenan contained therein while permitting hydration of the lambda plants in contact with the solution to proceed. The minimum concentration of cation required depends largely upon the pH and the temperature of the solution. The minimum cation concentration ranges upwardly from a minimum of 0.0025 molar at 5° C., for example in the case of potassium, to a minimum of 1.2 molar at 9°-5° C., both at a pH from 10 to 13. At 20° C. (room temperature), a frequently convenient temperature for carrying out the process, the minimum concentration of cation is 0.02 molar, for example in the case of calcium. While there is no critical upper limit on the cation concentration it is usually undesirable to employ concentrations above 0.2 molar because this tends to retard the rate of hydration of the lambda plants.

The hydration or increase in water content of the sea plants in accordance with the present invention should be carried out to the point where the carrageenan just begins to exude from the lambda plants but before substantial dissolution of the carrageenan in the surrounding water occurs, and at the same time before hydration of the kappa plants has proceeded to the same extent, and before substantial dissolution of the kappa or lambda carrageenan has occurred. To the extent that dissolution of carrageenan occurs during the hydration step the yield of lambda- or kappa-carrageenan from the plants after separation is decreased, so that it is desirable to avoid dissolution of more than about 5% by weight of the carrageenan during hydration. Moreover, separation of the lambda plants from the kappa plants becomes increasingly difficult with increasing hydration of the kappa plants, so that it is desirable to minimize hydration of the kappa plants as well as consequent dissolution of kappa-carrageenan for this reason also.

The pH of the water solution of cation affects the rate of hydration of kappa plants; if the pH drops below about 9, kappa plants tend to become hydrated to an undesirable extent. Since bone dry kappa plants are generally acidic in nature, immersion of such plants in the water solution containing a cation results in a decrease of the pH of the solution, requiring the addition of more base such as ammonium or potassium hydroxide or of calcium hydroxide (lime water) in order to maintain the pH in the desired range from 10 to 13. Within this range, an increase in pH of the solution results in only a moderate increase in the rate of hydration of lambda plants. In general, at least 0.02 g hydroxide ion is required per gram of bone dry plants. Although a pH above 13 can be used, even as high as 14, there is no advantage in exceeding a value of 13.

The anion present in the water solution may be any anion which does not decrease the solubility of the cation excessively. Hydroxides are useful in achieving the desired pH level and may be used either alone or in conjunction with soluble salts of different anions such as halides (e.g. chlorides), sulfates, carbonates, oxalates, acetates, or the like.

The speed or rate of hydration (absorption of water) of lambda plants is also dependent on the past history and treatment of the plants, as well as on the temperature, pH, and cation concentration of the water solution in which it is hydrated. Variations in harvesting methods, handling methods during initial drying, and in storage conditions affect the rate of hydration. If, for example, the seaplants were accidentally wetted by rain during the normal sun drying procedure, the time required for achieving the desired degree of lambda plant hydration under any given set of conditions would be decreased considerably. Similarly, if sea plants have been stored in a slightly damp state, the lambda hydration time would be decreased. Moreover, development of a compacted sticky characteristic in the lambda plants may not occur simultaneously with hydration but may require additional time. For example, after immersion of the mixture of sea plants in the water solution of cation produces absorption of even as much water as 8-10 times the bone dry weight of the plants it is found in some cases that not all of the lambda plants have developed compacted sticky or gummy characteristics but that these characteristics do develop if the solution is drained from the plants and they are simply allowed to stand in humid air or in contact with fresh water for some additional time, without drying out.

The relative amounts of sea plant and water solution of cation used may vary over a wide range, depending in part on the water content of the plants to be treated. In the case of bone dry plants it is usually desirable that the weight of water solution be at least 20 times the weight of the plants in order to ensure sufficient hydration within a reasonable time period, but as little as 10 times the weight of the plants can be used, particularly at higher temperatures. If the plants to be treated are freshly harvested, they will contain water amounting to 2-3 times their bone dry weight, so that the amount of water solution required for hydration is proportionately reduced. There is no upper limit on the proportion of water solution used except as dictated by convenience and economics. In practice, an amount of solution from 40 to 100 times the bone dry weight of the plants is most satisfactory. The temperature at which hydration is conducted can also vary widely, from about 5° to 95° C. Although higher temperatures can be used, this leads to the necessity of using pressure equipment which greatly increases the cost of the process. In general, all other conditions being kept constant, each increase in 10° C. in temperature results in a 50% decrease in the time required to reach a specific level of hydration. It should be noted, however, that although process times are shorter at elevated temperatures, the minimum concentration of cations required to prevent excessive hydration of kappa plants increases.

For any given sample of sea plants containing a mixture of kappa plants and lambda plants the approximate minimum time required for adequate hydration in decanted lime water (saturated calcium hydroxide solution) at pH 11.7 at 20° C. using 60 parts by weight of lime water for each part of bone dry plants can be determined by measuring the weight gain of a sample of the plants after 5 minutes immersion under the stated conditions. The approximate minimum total time in minutes (T) can then be calculated as follows:

$$T = 1125 - 370 \left( \frac{\text{wt. water content of plants}}{\text{Bone dry weight of plants}} \right)$$

Similar relationships can be established for other treatment conditions by simple experiment.

If the sea plants to be treated contain excessive amounts of dirt or entrained salt, they should not be washed with fresh water because it tends to lead to undue hydration of the kappa plants during the subsequent hydration step; instead, any wash water employed should contain one of the cations specified above.

It is desirable to monitor the extent of hydration during the course of the process in order to achieve optimum results. The total water content of the mixed plants can readily be determined at any given time simply by weighing a sample and subtracting its bone dry weight. However, in order to interpret this, it is necessary to carry out a preliminary analysis of the plant mixture to determine relative proportions of kappa and lambda plants. A suitable procedure for determining kappa plant content of a plant mixture is as follows:

Kappa Plant Content

A 50 g sample of damp mixed seaweed is dried in a circulating hot air oven at 70° C. and weighed in the bone dry state ($X_1$). The sample is then immersed in 500 ml of a water solution containing 3% potassium hydroxide, 10% potassium chloride at 90° C. for 1 hour. The solution is drained from the seaweed, and the weed is thoroughly washed in cold running water to remove all disintegrated lambda-bearing particles. The sample is dried in a laboratory oven at 70° C. until bone dry, and weighed ($X_2$).

% kappa-bearing plants = $(X_2 F / X_1) \cdot 100$ where F is a factor to compensate for weight changes in kappa in the above procedure. For *Chondrus Crispus* this factor is 1.11. The factors for other sea plants can readily be determined by simple experimentation. The lambda plant content of the mixture is determined by difference.

The optimum weight ratio of treated mixed plants to bone dry mixed plants to facilitate separation of lambda plants from kappa plants is given in the following table for plant mixtures containing varying proportions of lambda plants and kappa plants:

| Mixture | | Ratio |
|---|---|---|
| % kappa plants | % lambda plants | weight of immersed plants / bone dry weight of plants |
| 90 | 10 | 4.75 |
| 80 | 20 | 5.00 |
| 70 | 30 | 5.25 |
| 60 | 40 | 5.50 |
| 50 | 50 | 5.75 |
| 40 | 60 | 6.00 |
| 30 | 70 | 6.25 |
| 20 | 80 | 6.50 |
| 10 | 90 | 6.75 |

If the treatment with the water solution containing the specified cation is carried out until the above-specified weight ratio is achieved, most of the lambda plants will exhibit compacted sticky characteristics while the kappa plants retain their hard incompactible fronded characteristics. In order to ensure complete development of the desired characteristics by all of the lambda plants it may be desirable, after draining the solution from the plants, to allow them to stand for an additional period of time under conditions which do not permit substantial drying of the plants to occur, e.g. by maintaining the plants in a humid atmosphere or moistened with water.

The following specific examples are intended to illustrate more fully the nature of the invention without acting as a limitation upon its scope.

EXAMPLE 1

Twelve 50 g samples of dried *Chondrus Crispus* with known moisture contents from different harvesting areas of Prince Edward Island and New Brunswick, stored in different ways, were treated identically through the same procedure, each being immersed in 3 liters decanted limed water (pH 11.7) at room temperature for 5 minutes, after which it was drained and weighed; each was then immersed in 800 ml aqueous solution containing 0.5% sodium hydroxide and 1.5% potassium chloride (pH 12.7) at 60° C. for 4 minutes, followed by draining and weighing; finally each was immersed in the same 3 liters of decanted lime water at room temprature for 4 minutes, drained and weighed. Each sample was then hand sorted into those pieces of seaweed exhibiting fronded, springy characteristics and those showing sticky and compacted characteristics. Each of these fractions was tested as described above to determine the percentage kappa carrageenan-bearing plants.

The weights determined were recalculated in terms of the ratio of water to bone dry weed, correcting for initial moisture content.

Results are displayed in Table 1.

TABLE 1

| | Ratio water/bone dry weed after | | | | |
|---|---|---|---|---|---|
| Seaweed sample # | initial lime water soak 5 mins | immersion in 0.5% NaOH + 1.5% KCl @ 60° C. 4 mins | final lime water soak 4 mins | % kappa plants in fronded material | % kappa plants in sticky material |
| 1 | 2.40 | 3.33 | 4.68 | 100 | 1.3 |
| 2 | 2.63 | 5.56 | 6.36 | 99.3 | 2.5 |
| 3 | 2.51 | 3.63 | 4.81 | 100 | 0 |
| 4 | 2.55 | 4.36 | 6.09 | 100 | 0 |
| 5 | 2.43 | 3.69 | 5.25 | 100 | 0 |
| 6 | 2.86 | 5.12 | 6.47 | 100 | 0 |
| 7 | 2.44 | 3.49 | 4.37 | 92 | 0 |
| 8 | 2.86 | 6.65 | 8.22 | 100 | 4 |
| 9 | 2.79 | 4.65 | 6.59 | 100 | 0 |
| 10 | 2.73 | 5.28 | 6.57 | 98 | 2 |
| 11 | 2.86 | 5.51 | 6.28 | 100 | 0 |
| 12 | 2.32 | 3.24 | 3.65 | 92 | 0 |

This example shows that the process is applicable to *Chondrus Crispus* seaweeds harvested in different areas and exposed to various conditions prior to processing. The empirical relationship between the water absorption of the weed after a 5 minute immersion in lime water at room temperature, and the rapidity of overall hydration of predominantly the lambda weed can be observed, those samples with the higher water absorption in general displaying much higher water ratio after the procedure, indicating that a shorter time duration for the second (60° C.) immersion would have been preferable. Two samples with initial water absorptions on the lower side (Samples 7 and 12) were not treated optimally through this procedure, and some of the contained lambda plants had not yet developed their sticky compacted nature—these could have benefited from a slightly longer immersion time in the second bath.

EXAMPLE 2

Several 50 g samples of the same batch of *Chondrus Crispus* of Prince Edward Island origin were treated by a variety of procedures to assess the effect of cation concentration in the treatment solution, and the effect of prewashing or wetting in fresh water or in lime water. After each stage the mass of drained wet seaweed was weighed and the absorption of water calculated on a bone dry plant basis, as indicated in the following summary:

| Test | STEP 1 Initial wash procedure 3 liters | STEP 2 Composition of solution, conditions of hydration 0.8 liters | STEP 3 Final immersion 3 liters |
|---|---|---|---|
| 1 | none | 0.5% NaOH, 2% KCl @ 60° C. for 4 mins (pH 12.5) | Room temp decanted lime water 5 mins |
| 2 | none | 0.5% NaOH, 1.5% KCl @ 60° C. for 4 mins (pH 12.6) | Same as (1) |
| 3 | 5 min immersion in fresh water | Same as (2) | Same as (1) |
| 4 | 5 min immersion decanted lime water @ RT | Same as (2) | Same as (1) |
| 5 | Same as (4) | 0.5% NaOH, 0.75% KCl @ 60° C. for 4 mins | Same as (1) |
| 6 | 8 min immersion decanted lime water @ RT | 1.5% KCl in decanted lime water @ 60° for 4 mins (pH 12) | Same as (1) |

The treated seaweed from each test was sorted into a first fraction exhibiting a sticky compacted characteristic, and a second exhibiting the original fronded springy characteristics. Both fractions were tested for moisture content, and also tested to determine the percentage kappa-bearing plants. The results were as follows:

| Test # | Ratio water/bone dry weed after Step 1 | after Step 2 | after Step 3 | In Springy Fronded Material | In Compacted Material | % kappa in Fronded mat'l | % kappa in compacted material |
|---|---|---|---|---|---|---|---|
| 1 | — | 3.31 | 4.39 | 3.02 | 8.23 | 99 | 1 |
| 2 | — | 3.82 | 5.08 | 4.13 | 10.74 | 98 | 1 |
| 3 | 3.02 | 4.89 | 6.13 | 5.45 | 10.90 | 98 | 8 |
| 4 | 2.58 | 5.28 | 6.71 | 3.04 | 16.27 | 99 | 2 |
| 5 | 2.51 | 6.08 | 7.90 | 6.69 | 16.57 | Difficult to separate | |
| 6 | 2.93 | 3.73 | 4.82 | 3.53 | 10.85 | 95 | 0 |

These results illustrate the importance of the potassium ion concentration in retarding the hydration of the kappa plants, as can best be seen by comparing tests 1, 2 and 5:

| Test # | % KCl in Step 2 solution | Water absorption by kappa plants |
|---|---|---|
| 1 | 2.0% | 3.02 |
| 2 | 1.5% | 4.13 |
| 5 | 0.75% | 6.69 |

In test #5, hydration of the kappa-bearing plants was sufficient to cause considerable difficulty in visually distinguishing the two fractions on the basis of physical characteristics. Test 3 illustrates the need to use a solution containing a cation for initial contact with the seaweed (in this case lime water with a Ca++ concentration of 0.02 mol liter), especially if an initial washing step is required to remove sand and dirt. Use of fresh water, as in test #3, causes considerable hydration of the kappa-bearing plants, such that some are mistaken for lambda-bearing. A comparison of the results of tests 4 and 6 shows that the hydration rate of the lambda is affected by the alkalinity of the treatment solution (Step 2), the higher the alkalinity, the higher the rate of hydration of the lambda-bearing plants, and conversely the lower the alkalinity the higher the hydration rate of the kappa plants. Pre-immersion (i.e. Step 1) in any fluid causes higher rates of lambda hydration, thus for best results conditions should be adjusted to compensate.

EXAMPLE 3

Twelve 50 g samples of dried Chondrus Crispus with known moisture contents from different harvesting areas of Prince Edward Island and New Brunswick, sun dried and stored under varying conditions, were treated separately, each by immersion in 3 liters of decanted lime water (pH 11.7) at 20° C. At intervals of 30 minutes the seaweed was removed from the solution, excess water eliminated, the mass of wet seaweed weighed and then replaced in the treatment solution. When any sample reached a water content of 4.3 parts water per part dry weed, or above, it was removed from the treatment solution, weighed and hand sorted into those pieces of seaweed exhibiting the original fronded, springy characteristics, and those showing sticky compacted characteristics. Half of the fronded material and all the sticky material were tested to determine percentage kappa plants. The remaining half of the fronded material was maintained in a closed container, to keep it damp, for 4 hours, and then again examined and sorted if appropriate into fronded and sticky fractions. Each of these in turn was tested to determine percentage kappa plants.

The results are tabulated as follows:

TABLE 3

| Seaweed sample # | Ratio water to bone dry weed after (minutes) | | | | | | | | | % kappa in sticky material | | % kappa in fronded material | |
|---|---|---|---|---|---|---|---|---|---|---|---|---|---|
| | 5 | 30 | 60 | 90 | 120 | 150 | 180 | 210 | 240 | 270 | after soak | after storage | after soak | after storage |
| 1 | 2.74 | 3.16 | 3.45 | 4.22 | 4.84 | Removed | | | | | 1 | (Note 1) | 98 | 100 |
| 2 | 2.66 | 3.28 | 3.58 | 3.80 | 4.13 | 4.63 | Removed | | | | 2 | 0 | 96 | 100 |
| 3 | 2.88 | 3.97 | 4.33 | Removed | | | | | | | 0 | (Note 2) | 100 | 100 |
| 4 | 2.87 | 4.60 | Removed | | | | | | | | 1 | (Note 2) | 100 | 100 |
| 5 | 2.62 | 3.57 | 3.83 | 3.88 | 4.04 | 4.55 | Removed | | | | 0 | 1 | 95 | 100 |
| 6 | 2.32 | 2.78 | 2.90 | 3.36 | 3.41 | 3.81 | 4.05 | 4.39 | Removed | | 0 | 0 | 86 | 100 |
| 7 | 2.79 | 3.48 | 4.15 | 5.16 | Removed | | | | | | 2 | (Note 2) | 100 | 100 |
| 8 | 2.73 | 3.33 | 3.71 | 4.12 | 4.41 | Removed | | | | | 4 | (Note 1) | 98 | 100 |
| 9 | 2.87 | 3.74 | 4.20 | 4.34 | Removed | | | | | | 1 | (Note 2) | 100 | 100 |

TABLE 3-continued

| Seaweed sample # | Ratio water to bone dry weed after (minutes) | | | | | | | | | | % kappa in sticky material | | % kappa in fronded material | |
|---|---|---|---|---|---|---|---|---|---|---|---|---|---|---|
| | 5 | 30 | 60 | 90 | 120 | 150 | 180 | 210 | 240 | 270 | after soak | after storage | after soak | after storage |
| 10 | 2.40 | 2.73 | 2.90 | 3.10 | 3.53 | 3.81 | 4.01 | 4.30 | Removed | | 0 | 0 | 95 | 100 |
| 11 | 2.44 | 2.87 | 3.05 | 3.33 | 3.23 | 3.63 | 3.81 | 3.97 | 4.23 | 4.45 Removed | 0 | 0 | 82 | 98 |
| 12 | 2.91 | 3.21 | 3.33 | 3.91 | 4.35 | Removed | | | | | 0 | (Note 2) | 100 | 100 |

(Note 1): Insufficient sample to test
(Note 2): No sticky material after storage The results show that the 5 minute hydration level of the weed is an indicator of the overall time required to achieve a specific hydration level. It further illustrates that the process can be controlled by monitoring the weight gain of the seaweed. Those types of seaweed requiring a long immersion time, however, do not fully develop recognizable "lambda" characteristics, by the time the average hydration level reaches 4.3 parts water per part of dry weed as evidenced by the analysis of the fronded material after the immersion in lime water in Samples 6 & 11. This may be due to the normal statistical variation in any sample of seaweed, and there is no doubt that full development of the sticky characteristics of the lambda-containing plants would occur with longer immersion times; it is undesirable however to extend the immersion time in this case as some of the sticky material already present in the seaweed may start dissolving representing a loss of valuable product. Full development of the sticky characteristics in these cases can, however, be achieved without excessive dissolution of carrageenan by storage of seaweed in a damp state for a period of around 4 hours, as shown in Samples 6 & 11.

EXAMPLE 4

5 kg of wet, as-harvested *Chondrus Crispus*, drag-raked off Miminegash, Prince Edward Island, was immersed directly in 15 liters of a seawater slurry containing 4% hydrated lime by weight at pH 11.5. The seaweed remained in contact with the limed seawater for a period of 10 days at approximately 15° C. after which time the normal reddish color of Chondrus had changd to pale green, but the normally present extraneous seaweeds were still a brown color. The treated seaweed was removed from the limed seawater and washed by agitation in fresh seawater to remove lime particles and other inorganic contaminants. A portion of the wet treated seaweed (2.24 kg weight wet) was allowed to drain by gravity for 8 hours, the resultant water content of the seaweed being 75.2%. Seaweed other than *Chondrus Crispus*, being visually apparent, was removed by hand sorting; the wet weight of the remaining Chondrus in this 2.24 kg portion was then 1.99 kg, or equivalent to a calculated bone dry weight of 482 g.

Portions of this damp seawater lime slurry treated Chondrus were then immersed in plain cold fresh water for a period of 10 minutes, then removed and allowed to drain for 8 minutes. The seaweed was then placed on a flat surface, and the lambda carrageenan-bearing Chondrus was sorted out by hand, it being visually and physically distinguishable by its compacted gummy appearance. This immersion and selection procedure was repeated a further two times, the remaining Chondrus after removal of lambda being reimmersed in the same fresh water for 10 minutes, drained for 8 minutes and sorted into fractions.

From the 1.99 kg of clean damp Chondrus, the three operations yielded the following weights of wet lambda-bearing plant:

| | | |
|---|---|---|
| 1st immersion: | 975 gm | ⎫ |
| 2nd immersion: | 199 gm | ⎬ Average water content 88.6% |
| 3rd immersion: | 50 gm | ⎭ |

After the third immersion, the drained damp residual kappa plant weight was 1214 gm, with a water content of 82.0%.

A second portion of the original seaweed soaked in limed seawater was subjected to the procedure described above, i.e. draining, immersion in cold tap water for short periods, followed by further draining, but instead of sorting this material by hand, it was fed into an upward moving air stream in a cylindrical duct. The kappa plants, having retained their fronded nature, were buoyant, and were carried upwards by flotation in the air stream; whereas the lambda plants, because of their compacted nature, fell through the air stream to the bottom of the cylindrical duct.

Separation of lambda plants from kappa plants in other portions of the same material was achieved by impacting the material against a moist moving conveyor belt reach; at the end of the reach the kappa plants fell or were thrown off and the lambda plants were thereafter removed by scraping. Separation was also achieved by passing the material through the nip of a fish deboning machine having a perforated rotating drum; the lambda plants were extruded through the perforations while the kappa plants were not.

What is claimed is:

1. A method which comprises preferentially hydrating lambda-carrageenan-containing sea plants in admixture with kappa-carrageenan-containing sea plants without substantial dissolution of carrageenan, and
   separating said lambda plants from said kappa plants by selection based upon water content or upon properties related to or dependent on water content of said plants.

2. A method of separating kappa carrageenan from lambda carrageenan in a mixture of sea plants containing both kappa- and lambda-carrageenan which comprises maintaining a mixture of said plants in contact with a water solution at a pH above about 10 containing a cation selected from the group consisting of ammonium, potassium, rubidium, cesium, calcium, barium, strontium and magnesium at a temperature from 5° to 95° C., the initial concentration of said cation being at least 0.0025 molar, until said lambda plants exhibit compacted sticky characteristics while said kappa plants retain their hard incompactible fronded characteristics, and separating the lambda plants from the kappa plant by selection based on said characteristics.

3. A method which comprises contacting a mixture of kappa-carrageenan-containing and lambda-carrageenan-containing sea plants with a water solution at pH above about 10 containing a cation selected from the group consisting of ammonium, potassium, rubidium, cesium, calcium, barium, strontium and magnesium at a temperature from 5° to 95° C., the initial concentration of cation in said solution being above 0.0025 molar, until the water content of said lambda plants is from 4.5 to 15 times the bone-dry weight thereof and the water content of said kappa plants is no greater than 6 times the bone-dry weight thereof and less than that of said lambda plants, and separating the lambda plants from the kappa plants by selection based on water content.

4. A method as claimed in claim 3 in which the water content of said lambda plants is from 4.5 to 7 times the bone-dry weight thereof and that of the kappa plants is no greater than 4 times the bone dry weight thereof.

5. A method as claimed in any of claims 1, 2 or 3 in which said separating is carried out manually with visual inspection of said mixture.

6. A method as claimed in any of claims 1, 2 or 3 in which said cation comprises potassium.

7. A method as claimed in any of claims 1, 2 or 3 in which said cation comprises calcium.

8. A method as claimed in any of claims 1, 2 or 3 in which the mixture of kappa-carrageenan containing and lambda-carrageenan containing sea plants is *Chondrus Crispus*.

* * * * *

UNITED STATES PATENT AND TRADEMARK OFFICE
CERTIFICATE OF CORRECTION

PATENT NO. : 4,816,573
DATED : March 28, 1989
INVENTOR(S) : Whitaker

It is certified that error appears in the above-identified patent and that said Letters Patent is hereby corrected as shown below:

Column 1, lines 37-38, "tetras-porophytes" should be --tetra-sporophytes--
Column 1, lines 41-42, "tetras-porophytic" should be --tetra-sporophytic--
Column 2, line 58, "9°-5°C." should be --95° C.--
Column 5, line 5, "$(X_2F/X_1 \bullet 100$" should be --$(X_2F/X_1) \bullet 100$--
Column 12, line 8, delete "1"
Column 12, line 10, delete "1,"

Signed and Sealed this

Twenty-third Day of January, 1990

Attest:

JEFFREY M. SAMUELS

Attesting Officer    Acting Commissioner of Patents and Trademarks